(12) United States Patent
Impellizzeri et al.

(10) Patent No.: US 8,834,534 B2
(45) Date of Patent: Sep. 16, 2014

(54) SCAPHOLUNATE STABILIZATION IMPLANT

(75) Inventors: Frédéric Impellizzeri, Salon de Provence (FR); Patrick Houvet, Boulogne (FR)

(73) Assignee: Biotech Ortho, Salon de Provence (FR)

(*) Notice: Subject to any disclaimer, the term of this patent is extended or adjusted under 35 U.S.C. 154(b) by 375 days.

(21) Appl. No.: 13/499,017

(22) PCT Filed: Oct. 11, 2010

(86) PCT No.: PCT/FR2010/000681
§ 371 (c)(1),
(2), (4) Date: Jun. 18, 2012

(87) PCT Pub. No.: WO2011/045485
PCT Pub. Date: Apr. 21, 2011

(65) Prior Publication Data
US 2012/0245643 A1  Sep. 27, 2012

(30) Foreign Application Priority Data

Oct. 13, 2009 (FR) ...................................... 0904894

(51) Int. Cl.
*A61B 17/80* (2006.01)
(52) U.S. Cl.
CPC ......... *A61B 17/8061* (2013.01); *A61B 17/8085* (2013.01)
USPC ............ 606/283; 606/282; 606/285; 606/294

(58) Field of Classification Search
USPC .......................... 606/282–285, 294, 902–906
See application file for complete search history.

(56) References Cited

U.S. PATENT DOCUMENTS

| | | | |
|---|---|---|---|
| 5,690,631 A | 11/1997 | Duncan et al. | |
| 7,481,811 B2* | 1/2009 | Suh | ................. 606/71 |
| 8,317,841 B2* | 11/2012 | Bray, Jr. | ...................... 606/283 |
| 2005/0043732 A1* | 2/2005 | Dalton | .......................... 606/61 |
| 2005/0070904 A1 | 3/2005 | Gerlach et al. | |
| 2006/0241592 A1 | 10/2006 | Myerson et al. | |
| 2009/0036930 A1 | 2/2009 | Allison | |

FOREIGN PATENT DOCUMENTS

EP  1728480 A1  12/2006

OTHER PUBLICATIONS

International Search Report for corresponding International Application No. PCT/FR2010/000681.

\* cited by examiner

*Primary Examiner* — Andrew Yang
*Assistant Examiner* — Olivia C Chang
(74) *Attorney, Agent, or Firm* — Egbert Law Offices, PLLC

(57) ABSTRACT

A scapholunate stabilization graft is made up of an oblong plate, made of a material having a resilient deformation capability. The ends of the plate are provided with at least one hole enabling an attachment screw to pass therethrough, and the central portion of which has an opening defined by two opposite sides. A spring connects two remote points of said sides, said spring being placed along the diagonal within said opening.

9 Claims, 2 Drawing Sheets

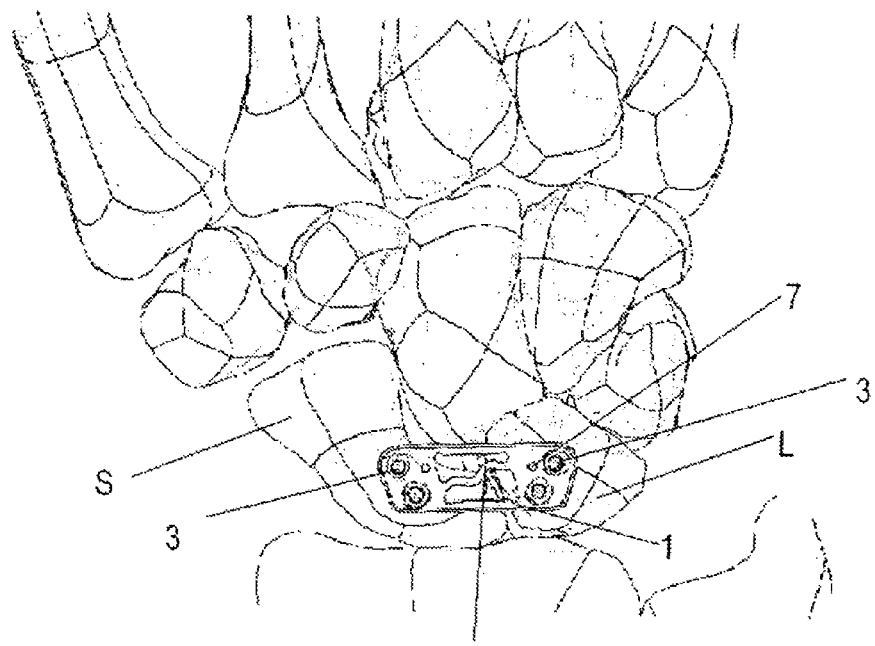
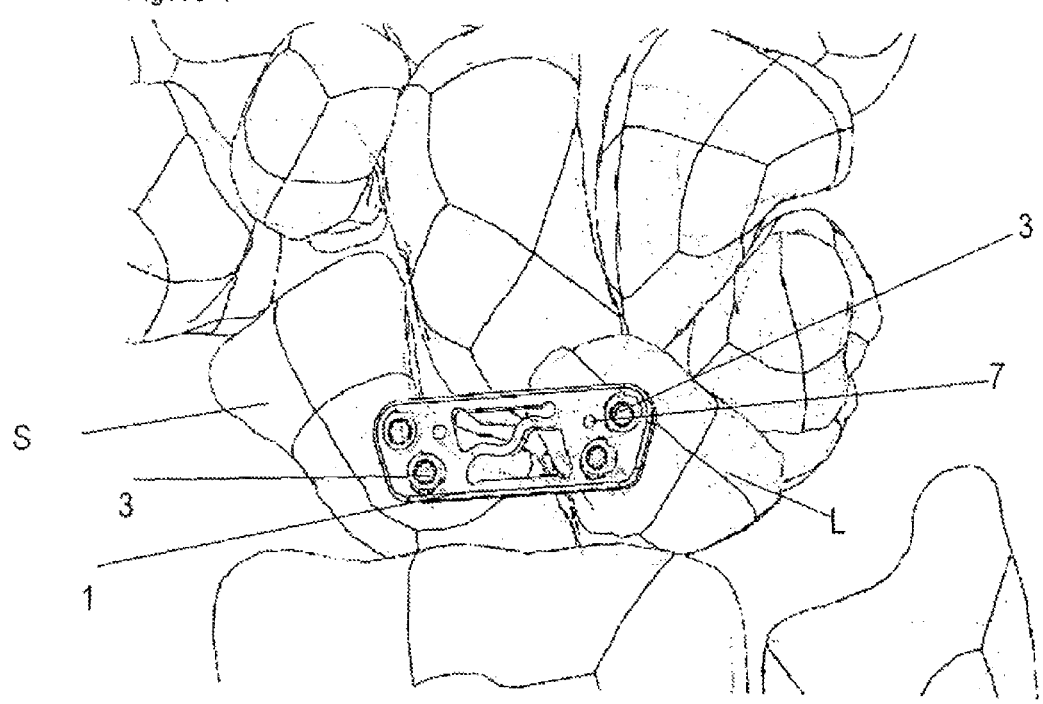

SCAPHOLUNATE STABILIZATION IMPLANT

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention concerns a scapholunate stabilization implant.

2. Description of Related Art Including Information Disclosed Under 37 CFR 1.97 and 37 CFR 1.98.

The scaphoid and the lunate bone are two of the eight bones constituting the carpus (wrist). During a severe fall involving a landing on the wrist, the ligament connecting these two bones called the scapholunate ligament is susceptible of sustaining lesions such as a laceration or a tear. The impairment of this ligament creates an instability which leads to premature osteo-arthritis.

If this lesion is tended to at an early stage by a surgeon, he can perform a suture which can only be contemplated if the ligament is still vascularized.

However, if the lesion is not promptly attended to, the damage caused by the rubbing of these two bones on each other may be irreversible and it will be necessary to envisage arthrodesis or even ablation of the two bones.

Also known are prosthetic devices which allow replacement of the scapholunate ligament.

Most often these devices consist of two plates intended to be anchored in each of the two bones to be connected, or fastened on the latter, and of a rod or wire making it possible to establish the connection of said two plates.

The drawback of such devices is that they generally are constituted, in part, of metallic elements. This means that there is a risk of bone adhesion. In effect, when a implant is present in the organism for an extended period, the bone tends to 'push back' on the implant and to partially cover it. It may then become impossible to remove it in its entirety which can be problematic, particularly during subsequent surgical interventions.

Furthermore, in most cases, the current devices require immobilization of the wrist with a splint or a plaster cast for a period of 6 to 8 weeks which prevents any early mobilization and leads to wrist stiffness.

One aim of the present invention is to provide orthopedic surgeons with a simple, flexible and resistant stabilization implant which makes it possible to achieve a mechanical connection between the scaphoid and the lunate which reproduces the role of the scapho-lunate ligament.

BRIEF SUMMARY OF THE INVENTION

According to the invention, this aim has been achieved by a stabilization implant that is apt to replace the broken scapholunate ligament or to reinforce the injured scapholunate ligament, this implant being constituted by an oblong plate made of a material capable of elastic deformation, the ends of which are provided with at least one hole for a fastening screw and whose central portion features an opening with two opposing sides, a spring of predetermined stiffness connecting two distant points, preferably two points opposite of said sides, this spring being positioned diagonally in said opening.

The device according to the invention offers several interesting advantages. In particular:
- to provide an implant which efficiently performs the functions of the scapholunate ligament;
- to enable fast and precise placement of this implant;
- to allow relative movement of the scaphoid and the lunate bone, which is to say physiological functioning of the wrist.

According to an advantageous application, the scapholunate stabilization implant is of a trapezoidal or approximately trapezoidal shape.

According to another characteristic disposition, the implant as per the invention features, in its central portion, a deformation zone of the shape of a parallelogram or approximately of a parallelogram.

According to another example of production, each end of the scapholunate stabilization implant is provided with two screw holes.

The implant according to the invention is remarkable in that it is provided with holes which permit the passage of temporary holding pins, placed near the holes for the fastening screws.

According to an important disposition of the invention, the portion of the implant constituting the spring has a wavy shape.

According to an advantageous method of production, the scapholunate stabilization implant is made of one single piece which represents a great simplification in particular during its manufacture.

According to a preferred method of production, the scapholunate stabilization implant is made of any biocompatible material which has the necessary sturdiness and elasticity.

According to an advantageous method of production, the implant according to the invention is made of polyetheretherketone (PEEK).

This material possesses very interesting mechanical characteristics, because they allow a great deal of deformation while ensuring a return to its original shape in balanced position. This material is furthermore advantageous in that it is radiolucent and that it sustains no osseous adhesions so that it can easily be removed, even after having remained in the organism for several years.

BRIEF DESCRIPTION OF THE DRAWINGS

The aforementioned aims, characteristics and advantages and still others will become more apparent in the following detailed description and the attached drawings in which:

FIG. 3 is a perspective view illustrating the wrist of the right hand on its upper side, provided with a stabilization implant according to the invention, positioned on the scaphoid and the lunate.

FIG. 4 is an analog view to FIG. 3, and shows another example of production of the implant according to the invention.

Figure 1:
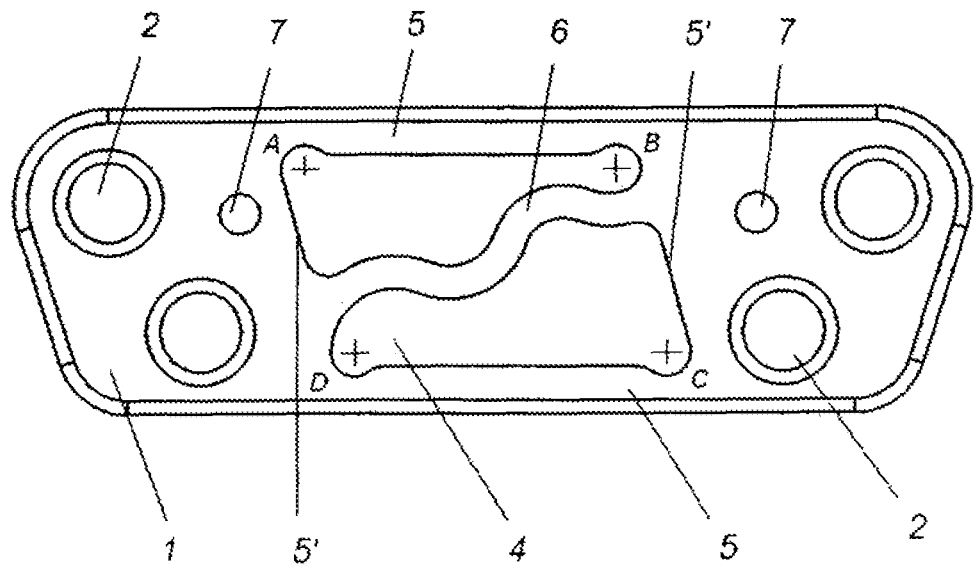
FIG. 1 is a top view of a first example of manufacture of the scapholunate stabilization implant, shown in a resting position.
Figure 2:
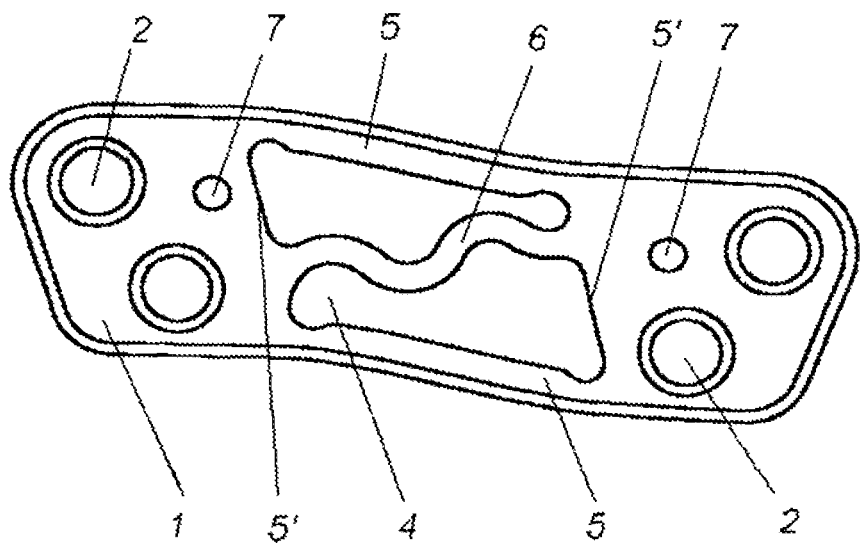
FIG. 2 is an analog view to FIG. 1, showing the implant as per the invention under a load.

Reference to said drawings is made to describe an interesting, although by no means limiting, example of manufacture of the scapholunate stabilization implant according to the invention.

DETAILED DESCRIPTION OF THE INVENTION

This scapholunate stabilization implant includes a plate 1 of oblong shape, made of a material capable of elastic deformation, the ends of which are provided with at least one hole 2 for passing through it a fastening screw 3 and the central portion of which features an opening 5, delimited by two opposing sides 5 or 5', a spring 6 linking together two distant points, for example two opposing points of said sides 5 or 5', this spring being placed along the diagonal in said opening 4.

According to the example shown, each end of the scapholunate stabilization implant 1 is provided with two spaced holes 2 for allowing fastening screws to pass through. These fastening screws 3 are preferably of the self-cutting, dual thread type being thus able to perform automatically, while they are being screwed in, the tapping of the holes 2 which are advantageously of a conical shape.

The length of the implant must be sufficient to permit the fastening of one of its ends on the scaphoid S and the fastening of its other end, on the lunate L.

It may for example measure about 20 mm in length and 10 mm in width.

As it is intended to be placed under the skin, the stabilization implant according to the invention is of a thin thickness, in the order of 1 to 1.5 mm, making it thereby practically undetectable under the upper surface of the skin.

The general shape of the implant is dictated by the anatomy of the bones.

According to a first method of production shown, the scapholunate stabilization implant is of a trapezoid or approximately trapezoid shape.

According to another method of production shown, the implant according to the invention has the shape of a parallelogram or approximately of a parallelogram.

The opening 4 present in the central portion of the implant has itself, and preferably so, the shape of a parallelogram or essentially of a parallelogram. This central portion constitutes a zone of deformation.

Depending on the shape of the opening 4, the length of the spring 6 varies. This makes it possible to have an influence on the stiffness of this spring and hence on the deformations allowed by the implant 1.

Other shapes may nevertheless be considered, especially to enable a left-hand utilization, and a right-hand utilization.

Advantageously the implant according to the invention is remarkable in that it is provided with at least one hole 7 for the passage of a temporary stabilization pin positioned in proximity of the holes 2 for the passage of the fastening screws 3.

In effect, before fastening the scapholunate implant 1 by means of the screws 3 in each of the two bones S and L concerned, the surgeon must first stabilize the implant in relation to these bones, then perform drillings in said bones for the positioning of said screws 3.

Preferably, for a better stabilization of the implant, each end of the implant is provided with two holes 7.

As per the example shown, the portion of the implant constituting the spring 6 has a wavy shape.

The implant is thus going to behave like a deformable parallelogram the stiffness of which is particularly affected by the geometry of the spring positions on one of the diagonals.

The mode of deformation of the scapholunate implant permits a relative displacement of bone S with respect to bone L while keeping them in contact or at a short distance.

Advantageously, the scapholunate stabilization implant 1 is manufactured of a single piece.

Therefore it is possibly advantageously produced using plastic injection techniques.

According to a preferred method of production, the scapholunate stabilization implant 1 is made of any biocompatible material featuring the sturdiness and elasticity that are necessary for it to fulfill its function.

Preferably and advantageously the implant 1 as per the invention is made of polyetheretherketone (PEEK).

We claim:

1. Scapholunate stabilization implant characterized in that it is constituted by a plate of oblong shape made of a material possessing the capacity for elastic deformation, the ends of which are provided with at least one hole for the passage of fastening screws and whose central portion has an opening delimited by two opposing sides or, a spring connecting two distant points of said sides, this spring being positioned along the diagonal in said opening.

2. Scapholunate stabilization implant as per claim 1, characterized in that each of its ends is provided with two holes for the passage of screws.

3. Scapholunate stabilization implant according to claim 1, characterized in that it is of trapezoid shape or of the shape of a parallelogram.

4. Scapholunate stabilization implant according to claim 1, characterized in that it features, in its central portion, an area of deformation in form of a parallelogram or approximately of a parallelogram.

5. Scapholunate stabilization implant according to claim 1, characterized in that it is provided with at least one hole for the passage of a temporary holding pin, positioned in proximity of the holes for the passage of fastening screws.

6. Device according to claim 1, characterized in that the portion of the implant which constitutes the spring has a wavy shape.

7. Scapholunate stabilization implant according to claim 1, characterized in that it is made of a single piece.

8. Scapholunate stabilization implant according to claim 1, characterized in that it is made of any biocompatible material possessing the necessary sturdiness and elasticity.

9. Scapholunate stabilization implant according to claim 1, characterized in that it is made of polyetheretherketone (PEEK).

* * * * *